(12) United States Patent
Robinson et al.

(10) Patent No.: US 9,962,284 B2
(45) Date of Patent: May 8, 2018

(54) THERMAL TREATMENT DEVICE

(75) Inventors: Ronni L. Robinson, Ambler, PA (US);
Harry S. Sowden, Glenside, PA (US);
Leo B. Kriksunov, Glenside, PA (US)

(73) Assignee: Johnson & Johnson Consumer Inc.,
Skillman, NJ (US)

( * ) Notice: Subject to any disclaimer, the term of this patent is extended or adjusted under 35 U.S.C. 154(b) by 1049 days.

(21) Appl. No.: 12/339,160

(22) Filed: Dec. 19, 2008

(65) Prior Publication Data

US 2009/0163984 A1   Jun. 25, 2009

Related U.S. Application Data

(60) Provisional application No. 61/014,802, filed on Dec. 19, 2007.

(51) Int. Cl.
| | |
|---|---|
| *A61F 7/00* | (2006.01) |
| *A61F 7/02* | (2006.01) |
| *A61H 7/00* | (2006.01) |
| *A61F 7/03* | (2006.01) |
| *A61H 23/02* | (2006.01) |
| *A61H 15/00* | (2006.01) |

(52) U.S. Cl.
CPC ............... *A61F 7/02* (2013.01); *A61H 7/00* (2013.01); *A61F 7/034* (2013.01); *A61F 2007/0071* (2013.01); *A61F 2007/0075* (2013.01); *A61F 2007/0078* (2013.01); *A61F 2007/0086* (2013.01); *A61F 2007/0228* (2013.01); *A61F 2007/0296* (2013.01); *A61H 23/02* (2013.01); *A61H 23/0254* (2013.01); *A61H 2015/0042* (2013.01); *A61H 2201/0173* (2013.01); *A61H 2201/0207* (2013.01); *A61H 2201/0214* (2013.01); *A61H 2201/0242* (2013.01); *A61H 2201/0257* (2013.01); *A61H 2201/0278* (2013.01); *A61H 2201/102* (2013.01); *A61H 2201/165* (2013.01); *A61H 2201/1626* (2013.01); *A61H 2201/1688* (2013.01); *A61H 2205/081* (2013.01)

(58) Field of Classification Search
USPC ...... 119/653, 654; 2/169, 247, 252; 607/108
See application file for complete search history.

(56) References Cited

U.S. PATENT DOCUMENTS

| | | | | |
|---|---|---|---|---|
| 912,527 | A | * | 2/1909 | Batter ............................ 126/204 |
| 1,539,299 | A | * | 5/1925 | Cheney ............................ 601/20 |
| 1,703,811 | A | | 2/1929 | Blum |

(Continued)

FOREIGN PATENT DOCUMENTS

| | | |
|---|---|---|
| CA | 2577939 A1 | 4/2006 |
| CH | 245959 A | 12/1946 |

(Continued)

OTHER PUBLICATIONS

International Search Report for PCT/US2008/087603 dated Apr. 9, 2009.

(Continued)

*Primary Examiner* — Scott Medway

(57) ABSTRACT

The present invention is directed to a reusable pain relieving treatment device, such as a belt, that comprises one or more conductive members that extend from an inner surface of the device and are capable of transferring heat, cold or vibrations from disposable or reusable packs.

9 Claims, 5 Drawing Sheets

(56) References Cited

U.S. PATENT DOCUMENTS

| | | | |
|---|---|---|---|
| 3,170,459 A * | 2/1965 | Phipps et al. | 600/391 |
| 3,327,713 A * | 6/1967 | Eidus | 607/96 |
| 4,242,715 A * | 12/1980 | Laird | 361/232 |
| 4,259,965 A * | 4/1981 | Fukuda et al. | 600/392 |
| 4,479,495 A * | 10/1984 | Isaacson | 606/204 |
| 4,592,358 A * | 6/1986 | Westplate | 607/112 |
| 4,685,442 A * | 8/1987 | Cieslak | 126/204 |
| 4,702,235 A * | 10/1987 | Hong | 602/13 |
| 4,846,176 A | 7/1989 | Golden | |
| 5,023,430 A * | 6/1991 | Brekkestran et al. | 219/486 |
| 5,179,942 A | 1/1993 | Drulias | |
| 5,302,806 A * | 4/1994 | Simmons et al. | 219/211 |
| 5,312,350 A * | 5/1994 | Jacobs | 604/116 |
| 5,336,255 A * | 8/1994 | Kanare et al. | 607/149 |
| 5,445,647 A * | 8/1995 | Choy | 606/204 |
| 5,484,366 A | 1/1996 | Wilkinson | |
| 5,534,021 A | 7/1996 | Dvoretzky et al. | |
| 5,605,144 A | 2/1997 | Simmons et al. | |
| 5,665,057 A * | 9/1997 | Murphy | 602/19 |
| 5,695,520 A * | 12/1997 | Bruckner et al. | 606/204 |
| 5,741,318 A | 4/1998 | Ouellette | |
| 5,800,490 A | 9/1998 | Patz | |
| 5,848,981 A * | 12/1998 | Herbranson | 601/134 |
| 5,918,590 A | 7/1999 | Burkett et al. | |
| 5,925,072 A | 7/1999 | Cramer et al. | |
| 5,928,275 A * | 7/1999 | Yates et al. | 607/112 |
| 6,074,413 A | 1/2000 | Davis et al. | |
| 6,027,521 A | 2/2000 | Ourada | 606/204 |
| 6,065,154 A * | 5/2000 | Hulings et al. | 2/102 |
| 6,102,875 A * | 8/2000 | Jones | 601/113 |
| 6,146,342 A | 11/2000 | Glen | |
| 6,206,909 B1 * | 3/2001 | Hanada et al. | 607/108 |
| 6,309,273 B1 * | 10/2001 | Kim | 446/28 |
| 6,409,748 B1 | 6/2002 | DeCarlo et al. | |
| 6,416,534 B1 | 7/2002 | Montagnino et al. | |
| 6,419,650 B1 * | 7/2002 | Ryan et al. | 601/122 |
| 6,425,913 B1 * | 7/2002 | Chao | 607/108 |
| 6,497,720 B1 * | 12/2002 | Augustine et al. | 607/96 |
| 6,549,411 B1 * | 4/2003 | Herbert | 361/704 |
| 6,567,696 B2 * | 5/2003 | Voznesensky et al. | 607/3 |
| 6,623,419 B1 | 9/2003 | Smith et al. | |
| 6,711,750 B1 * | 3/2004 | Yoo | 2/338 |
| 6,840,955 B2 * | 1/2005 | Ein | 607/108 |
| 7,077,858 B2 | 7/2006 | Fletcher et al. | |
| 7,147,610 B2 | 12/2006 | Maalouf | |
| D559,473 S * | 1/2008 | Nguyen | D30/152 |
| 7,399,484 B2 | 7/2008 | Ellefson et al. | |
| 7,637,883 B2 * | 12/2009 | Nyi | 602/21 |
| 7,781,051 B2 * | 8/2010 | Burr et al. | 428/221 |
| 7,889,502 B1 * | 2/2011 | Reis et al. | 361/717 |
| 8,021,406 B2 * | 9/2011 | Cazzini et al. | 607/104 |
| 2002/0086204 A1 * | 7/2002 | Rock et al. | 429/120 |
| 2002/0156509 A1 * | 10/2002 | Cheung | 607/96 |
| 2003/0014096 A1 | 1/2003 | Burkhart | |
| 2003/0125648 A1 * | 7/2003 | Leason et al. | 601/15 |
| 2004/0082886 A1 | 4/2004 | Timpson | |
| 2004/0217325 A1 | 11/2004 | Usui et al. | |
| 2005/0049526 A1 | 3/2005 | Baer | |
| 2005/0065581 A1 | 3/2005 | Fletcher | |
| 2005/0145372 A1 | 7/2005 | Noel | |
| 2006/0002988 A1 | 1/2006 | Ellefson et al. | |
| 2006/0100558 A1 | 5/2006 | Smith | |
| 2006/0258962 A1 | 11/2006 | Kopanic et al. | |
| 2007/0106356 A1 | 5/2007 | Carstens | |
| 2009/0222072 A1 | 9/2009 | Robinson et al. | |
| 2010/0161014 A1 | 6/2010 | Lynch et al. | |

FOREIGN PATENT DOCUMENTS

| | | | | |
|---|---|---|---|---|
| DE | 4410702 A1 | 10/1995 | | |
| EP | 1332740 A2 | 8/2003 | | |
| EP | 1332741 A | 8/2003 | | |
| EP | 1649841 A1 | 4/2006 | | |
| FR | 2408344 A | 6/1979 | | |
| FR | 2708196 A1 * | 7/1993 | | A61F 7/00 |
| GB | 2353711 A | 3/2001 | | |
| JP | 10099408 A * | 4/1998 | | A61H 39/04 |
| KR | 20-0315-273 | 6/2003 | | |
| RU | 2093117 C1 | 10/1997 | | |
| RU | 28954 U1 | 4/2003 | | |
| WO | WO 97/01312 A2 | 1/1997 | | |
| WO | WO 2005/110330 A | 11/2005 | | |
| WO | WO 2008/006018 A2 | 1/2008 | | |
| WO | WO 08/072099 A1 | 6/2008 | | |
| WO | WO 2009/108611 A1 | 9/2009 | | |

OTHER PUBLICATIONS

International Search Report for PCT/US2009/034945 dated Jul. 13, 2009.

European Search Report for EP 09252880.1 dated Apr. 19, 2010.

* cited by examiner

THERMAL TREATMENT DEVICE

CROSS REFERENCE TO RELATED APPLICATIONS

This application claims priority of the benefits of the filing of U.S. Provisional Application Ser. No. 61/014,802, filed Dec. 19, 2007. The complete disclosures of the aforementioned related U.S. patent application is/are hereby incorporated herein by reference for all purposes.

BACKGROUND OF THE INVENTION

The application of heat to the skin as a means to penetrate deeper into tissues has historically been used for pain relief of muscles and joints, as well as for the treatment of certain inflammatory conditions. The application of cold materials to the skin has also been used for similar treatments, especially for treating inflammatory responses such as joint inflammation.

Traditional heating devices have, in some instances, generated heat using chemical formulations, such as iron powder formulations, that oxidize when exposed to air. Commercially available thermal chemical formulation products are usually confined to disposable heat patches, which are available as loosely formed fabric bags filled with the exothermic composition. An alternate means of providing heat is by way of electrical heating elements that are attached to a power source. Since the desired time of use is often longer than 4 hours, in the case of an electrical source, the power source typically used in these types of devices is either an electrical wall outlet or a battery.

Other chemical heating devices include those products that incorporate heating portions into fabrics that can conform or are shaped to fit various parts of the body, such as the knee or the back as shown in U.S. Pat. No. 6,074,413. In these cases, typically the entire product, including the garment and the heat providing exothermic formulation materials, are disposable because they are incorporated into a unitary product. The chemical heating portion is not removable from such a unitary product, and therefore, the entire device is designed to be disposed following use. Each use can typically last for 6 to 12 hours, and a user may use 2-3 of these products over a 24-hour period. These types of products have the disadvantage of contributing to excess waste of material and higher cost since each use involves the use of an entire product form. In addition, these devices often have a layer of fabric, which is non-conductive, in-between the heat portion and the skin.

Other types of devices, such as those shown in U.S. Pat. No. 5,484,366, exemplify elements that are not disposable, such as using a back belt with gel pack containers. In such a device the gel-packs must be manually re-heated or cooled, taking more active participation by the user in order to be reusable. Similarly, the device shown in U.S. Pat. No. 6,416,534 uses a back belt with a flexible fabric, and a gel pack that is reheated using electrical heat. This type of device also involves active participation on the part of the user and a potential lag time in order to heat the gel-pack. U.S. Pat. No. 6,074,413 is directed to a disposable thermal back wrap having one or more thermal packs comprising a plurality of heat cells, wherein heat is applied to specific areas of the user's back, for pain relief. U.S. Pat. No. 5,605,144 is directed to a heating garment with pouch for accommodating inserted chemical heating packets that are air activated.

U.S. Pat. No. 5,484,366 is directed to an aerobic/cross training exercise belt. The belt comprises a straight piece of material having a fastener on each end whereby the ends can be fastened together to form a closed belt. A back lumbar support is connected to the rear body of the belt. The back lumbar support has at least one pocket to mount chemical gel-packs whereby the user would have a thermal application to the lumbar area while wear wearing the belt. The gel packs can be heated or cooled to the desired temperature. U.S. Pat. No. 6,623,419 is directed to a therapeutic back belt and related method of manufacture. The belt includes magnets that are secured to the belt and thermally active gel material. U.S. Pat. No. 5,179,942 is directed to a lumbar support therapeutic heat/cooling/air belt. The support has one pocket in the lower back section that is capable of receiving a packet to create a thermal change or provide air for support purposes.

Additional devices have also been disclosed, as shown in U.S. Pat. No. 7,147,610, that incorporate massaging elements with the heating elements so that they are conveniently available in a single device. Such a device involves excess bulk, is non-discreet and requires the use of external power sources (i.e. a junction box) since the heating and massaging element require the use of electrical power. In addition, although the parts are reusable, electrical elements tend to be non-washable. Published U.S. Patent Application 2004/0082886 is directed to a therapeutic device for relieving pain and stress in the hands and feet. The portable device provides heat and vibratory therapies for the hand or foot.

U.S. Pat. No. 6,146,342 is directed to massage pad having a plurality of randomly actuated pressure inducing elements. The apparatus massages the body by subjecting the body to impacts from reciprocating plungers. The plungers are secured in a flat array within a flexible pad. Each plunger has an associated solenoid device that alternately causes the plunger to project from the pad and to retract within the pad. An electrical circuit includes a power cord and plug assembly, manual controls disposed serially on the cord and plug assembly, and a controller generating operating signals randomly to the solenoids. A heating element is optionally included in the flexible pad, with a suitable controller provided among the controls.

Still other types of devices, as shown in U.S. Pat. No. 7,077,858, include those that use flexible heat exchangers to distribute cooling and heating agents to the skin utilizing electrical heat. U.S. Pat. No. 6,409,748 is directed to a heating pad with removable gel pack that provides rapid initial warming. U.S. Pat. No. 4,846,176 is directed to a thermal bandage having a conformable region that can be placed against the skin to uniformly heat or cool the contacted skin area.

SUMMARY OF THE INVENTION

The present invention described herein is a device which incorporates the elements of: being conductive against the skin; having both a reusable portion and a disposable portion; washable; portable; discreet; and minimal user involvement to get fast relief from the heating element. As used herein, "belt" is defined as a belt, sleeve, wrap, or garment for use on a part of an animal or human body.

DETAILED DESCRIPTION OF THE INVENTION

The first part of the device of this invention is in the form of an elastic back belt, sleeve, wrap, or garment (hereinafter "belt") which can be washable and reusable, and is capable of being set on a wearer's body. In one embodiment the belt is adapted to be wrapped around an individual's back for thermal treatment of back pain. In another embodiment the belt, sleeve or wrap is adapted to be wrapped around the individual's leg, foot, ankle, arm, elbow or shoulder. The belt is capable of accepting simultaneously or sequentially, several types of thermal packs, both for cooling and for heating, and therefore has a plurality of pockets into which the packs can be added. Therefore, in one embodiment the belt is reusable and the packs are disposable. In another embodiment, the belt is reusable, and at least some thermal packs are also reusable.

Thermally conductive members are exemplified by rotating members of round, elongated, ellipsoidal, cylindrical, or similar shape, including balls, ball bearings, or roller bearings on the side interfacing to human body, as shown in FIGS. 1, 2, 3, and 4. Rotating members with round edges are able to move independently and provide enhanced massage while simultaneously transferring thermal energy to the individual's body. The thermally conductive members are in contact with the body of the user, either directly contacting the skin, or contacting the body through clothing or garments worn by the user. Simultaneously the thermally conductive members are in contact with the thermal packs, either directly, or through supporting elements. Supporting elements or sockets are installed in the belt and are engaging and retaining the rotating thermally conductive members within the belt while providing for the ability of the thermally conductive members to rotate. The rotating members are adapted to rotate within the supporting elements or sockets due to shifts in the position of the belt on the body and thus provide for massaging treatment of the user's body.

Figure 1:
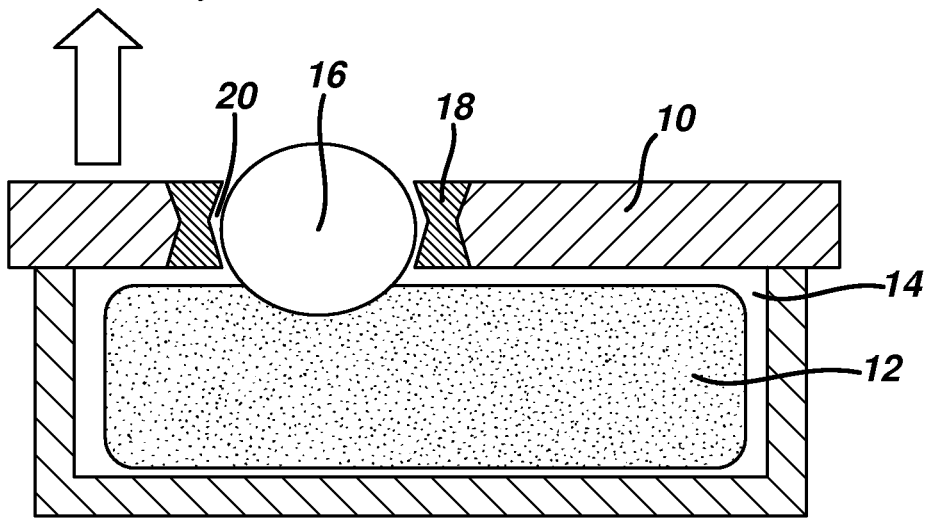
FIG. 1 is a side view of a treatment belt having a thermal pack and a rotating thermally conductive member.
Figure 2:
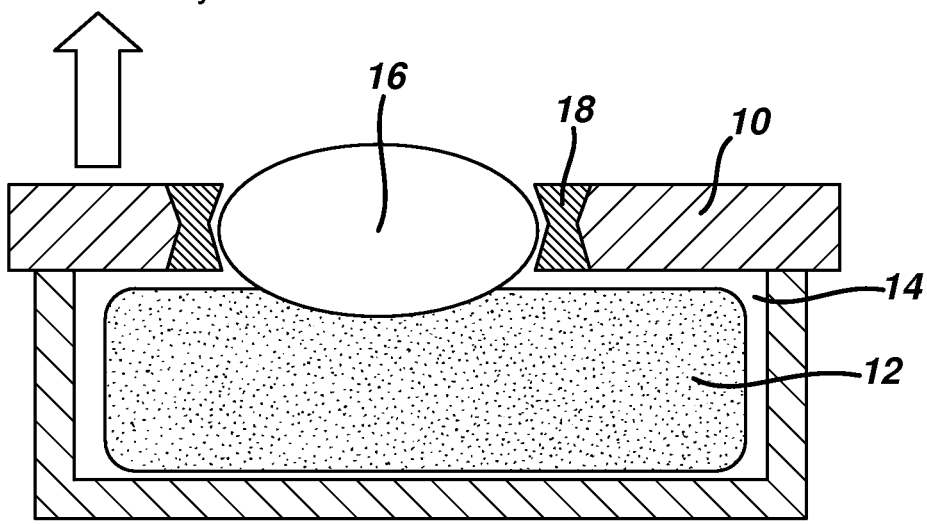
FIG. 2 is a side view of a thermal treatment belt having a thermal pack and an elliptical rotating thermally conductive member.
Figure 3:
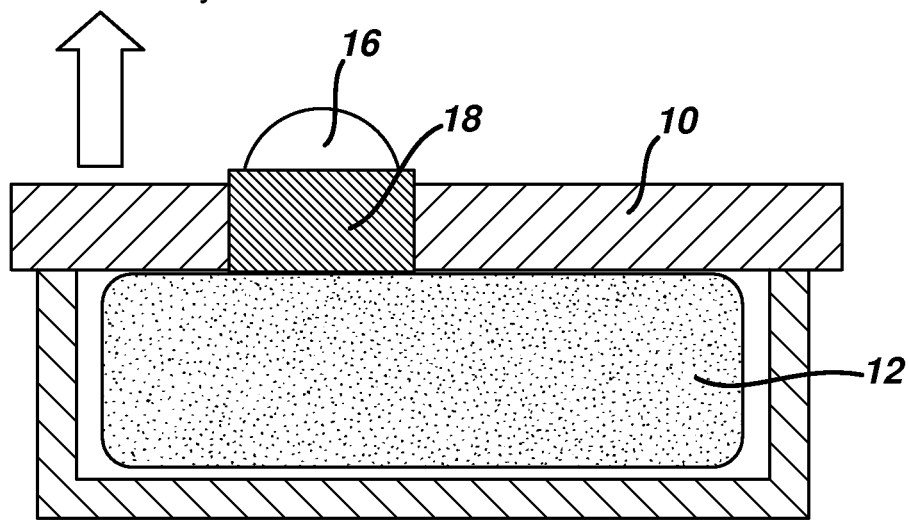
FIG. 3 is a side view of a thermal treatment belt having a thermal pack and a rotating thermally conductive member, wherein a supporting element completely surrounds the rotating member.
Figure 4:
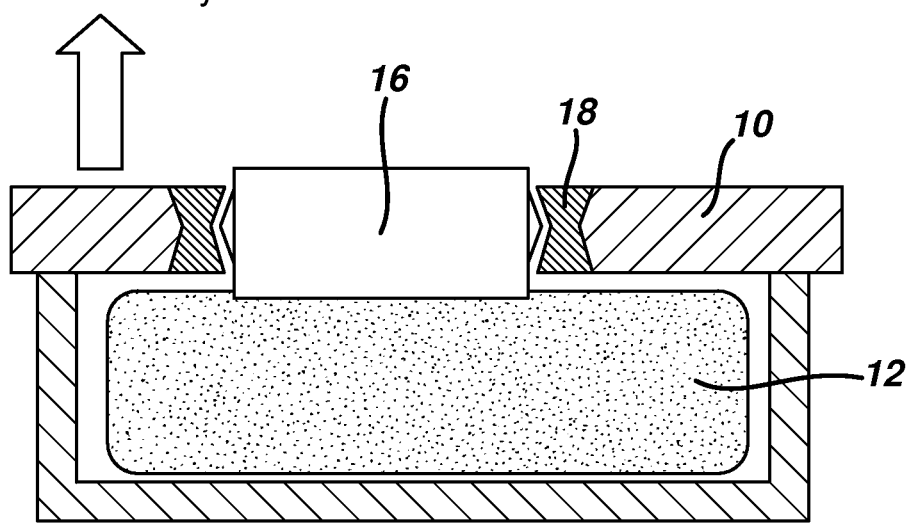
FIG. 4 is a side view of a thermal treatment belt having a thermal pack and a cylindrical rotating thermally conductive member, where two faces of the member are flat.

One such embodiment of the invention is illustrated in FIG. 1. Thermal treatment belt 10 includes a thermal pack or retainer 12 in a cell or cavity 14 and one or more rotating thermally conductive members 16 that are held in position with a supporting element 18. The supporting element can be made of plastic, metal or rubber and generally consists of a concentric ring that is designed to hold a circular object (such as a metal ball), without allowing it to fall out of the support. The supporting element partially obscures portions of the rotating member, but allows a certain portion to be exposed. Rotating members 16 rotate within a space or gap 20 provided between supporting elements 18 due to shifts in the position of the belt 10 on the body and thus provide for massaging treatment of the user's body. Another embodiment of the present invention is shown in FIG. 2 wherein the rotating thermally conductive member 16 has an elliptical profile. As shown in FIG. 3, supporting element 16 can completely surround rotating member 14. FIG. 4 shows thermal treatment belt 10 comprising a thermal pack 12 and a cylindrical rotating thermally conductive member 16, where at least two faces of conductive member 16 are flat.

In another embodiment, the belt has thermally conductive members protruding from the side of the belt containing the pockets to the side that is in contact with the skin. These thermally conductive members are evident as bulges or protrusions on one side of the belt that are directed towards the skin upon application of the belt. The thermally conductive members deliver thermal energy (heat or cold) to the individual's skin and simultaneously provide massaging action on contact with the skin. The thermally conductive members serve to effectively transfer or re-distribute heat or cold from the thermal packs to the individual's body. In addition, thermally conductive members create a non-uniform thermal sensations on the body or on the skin in case of direct application to skin, whereby body or skin areas in immediate contact with the thermally conductive members experience much stronger sensations of heat or cold relative to the adjacent areas.

Figure 5:
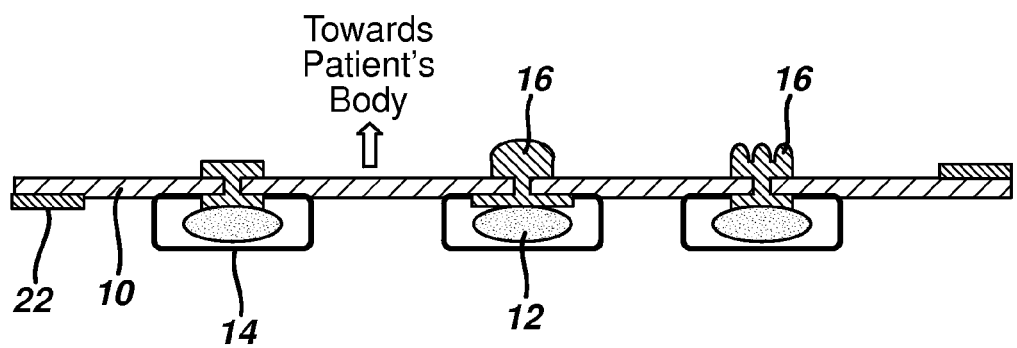
FIG. 5 is a side view of a thermal treatment belt having multiple thermal packs and thermally conductive metal members.
Figure 6:
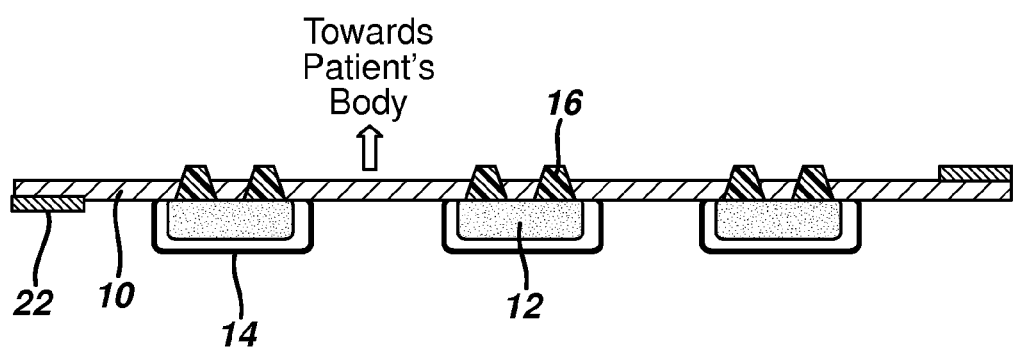
FIG. 6 is a side view of a thermal treatment belt having multiple thermal packs and thermally conductive rubber members.

FIG. 5 shows a thermal treatment belt 10 comprising multiple thermal packs 12 and thermally conductive members 16. Thermal packs 12 are held in pockets that define cavities 14. Thermally conductive members 16 are shown in multiple shape configurations. Securing means 22, such as a snap or button, can be provided on thermal treatment belts 10 of the present invention. FIG. 6 shows a thermal treatment belt 10 having multiple thermal packs 12 and thermally conductive members 16, wherein thermally conductive members 16 are comprised of rubber or other elastomeric material. Thermal packs 12 are held in pockets that define cavities 14.

Figure 7:
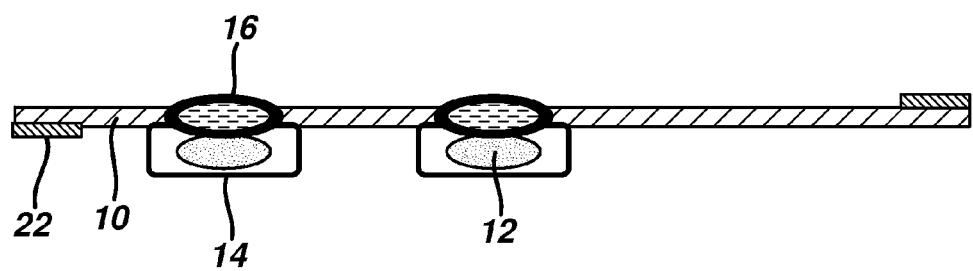
FIG. 7 is a side view of a thermal treatment belt having multiple thermal packs and thermally conductive liquid-filled members.

In one embodiment, the thermally conductive members comprise a sealed portion containing a liquid such as water, a buffer or a fatty acid such as silicon or mineral oil. In this embodiment, the liquid facilitates the transfer of the thermal energy from the thermal pack through the thermally conductive member. In one embodiment the fatty acid contained in the thermally conductive member is such that the melting point is above the temperature at which the thermal pack delivers heat, allowing for the fatty acid to melt and re-solidify upon reuse. FIG. 7 shows a thermal treatment belt 10 comprising multiple thermal packs 12 and thermally conductive members 16, wherein thermally conductive members 16 are liquid (water or oil) filled pouches.

In one embodiment, the belt has thermally conductive fabric areas in order to deliver the heat from the pack in the pocket to the side of the belt that is in contact with the skin. The thermally conductive members can be constructed of a thermally conductive fabric that contains at least some portion of metal or graphite, including metal wires, metal or metal-coated yarn, graphite fibers, graphite tapes, flakes, paint, polymer coatings impregnated with metal, ironed on metal powder coatings, or metal foils attached to the fabric using an adhesive.

Figure 8:
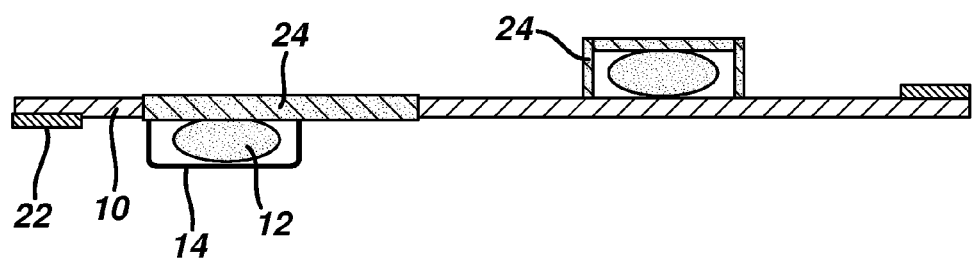
FIG. 8 is a side view of a thermal treatment belt having multiple thermal packs wherein the pockets for holding the thermal packs or a portion of the belt include heat conductive fabrics.
Figure 9:
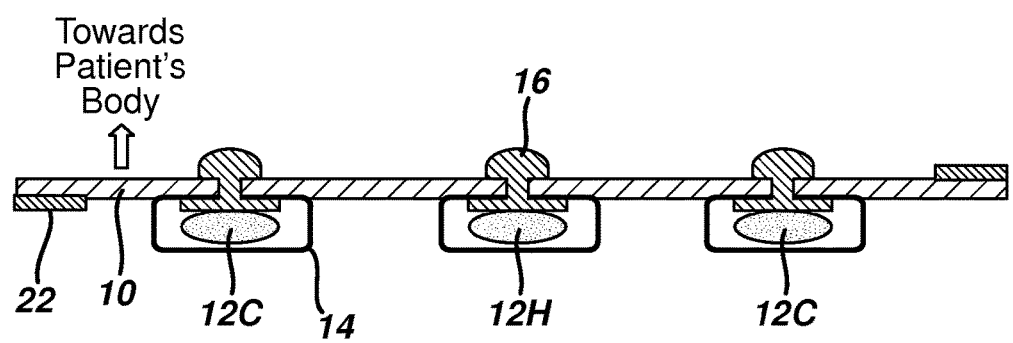
FIG. 9 is a side view of a thermal treatment belt having multiple thermal packs and thermally conductive members, where the thermal packs alternate between cooling packs and heating packs.

FIG. 8 shows a thermal treatment belt 10 comprising multiple thermal packs 12 where the pockets form cavities 14 for holding individual thermal packs 12 or a portion of belt 10 is made from heat conductive fabrics 24. FIG. 9 shows a thermal treatment belt 10 comprising multiple thermal packs 12 and thermally conductive members 16, where thermally conductive members 16 are shown as rivets, and thermal packs 12 are arranged by alternating between cooling packs 12C and exothermic heating packs 12H.

Advantageously and beneficially, the space around the thermally conductive members is available for removal and evaporation of sweat and provides for areas of the body or skin not in contact or not covered by any implement. Additionally, thermal contrast delivered to the body can be much higher whereby thermally conductive members transferring heat and transferring cold can be immediately adjacent to each. This is also achieved without significant losses of thermal energy due to heat transfer.

The thermally conductive members may be constructed of metals such as aluminum, iron, metal alloys, silver, copper or steel, or metallic alloys, or non-metallic thermally conductive materials such as carbon-based materials, including graphite, glassy carbon or similar, as well as of metal-containing or carbon-containing composite materials, such as metal-filled polymers or graphite-filled polymers. In one embodiment the thermally conductive members are constructed of thermally conductive plastics, polymers, fabrics or rubber. Optionally, these thermally conductive members may contain wires or fibers comprising the metals described above in order to make them more thermally conductive.

In one embodiment, the thermally conductive members comprise a material such as a fragrance or other liquid that vaporizes upon heating, which may deliver steam heat or a fragrance.

In one embodiment, the thermally conductive members are designed in the shape of rivets or pins that are exposed on the side of the belt in contact with the individual's body or with the individual's skin. Contact with the body can be established either directly with the thermally conductive members touching the skin, or with the thermally conductive members touching a garment that is disposed over the individual's body. One face of the rivet or pin is in contact with skin and the opposite face of the rivet or pin is in contact with the thermal pack that is inserted into the pocket of the belt. The rivets or pins are fixed and not removable by the individual as part of the reusable belt, and are incorporated into the fabric. Multiple rivets or pins may be in contact with each thermal pack and in one embodiment 2 pins are in contact with a single thermal pack, e.g. 3 pins per single thermal pack, e.g. 5 pins per single thermal pack, e.g. 6 pins per single thermal pack. In one embodiment the dimensions of the thermally conductive member on the side of the belt in contact with the skin is from about 2 millimeters to about 77 millimeters, or from about 5 millimeters to about 50 millimeters, or from about 5 millimeters to about 30 millimeters.

The height by which the thermally conductive members such as rivets or pins are protruding over the substantially flat surface of the belt on the side of the belt facing the individual's body is from about 1 millimeter to about 25 millimeters. In one embodiment, the thermally conductive members are protruding by about 5 millimeters or by about 10 millimeters above the surface of the belt. In one embodiment, all thermally conductive members have the same height, while in another embodiment, some thermally conductive members are higher and some are lower, for example some thermally conductive members are 3 millimeters high, some are 5 millimeters high, and some are 8 millimeters high.

According to an embodiment of the present invention, thermally conductive members are shaped so as to effectively collect thermal energy from thermal packs and to effectively transfer thermal energy to the individual's body. In one embodiment, thermally conductive members are shaped as two substantially flat round or elongated disks interconnected by a cylindrical element, with first disk in contact with the thermal pack and the second disk interfacing with the individual's body. In one embodiment the disk having contact with a thermal pack has a larger surface area than the disk that is in contact with the individual's body. In this case the thermal energy is advantageously collected from the thermal pack and then transferred to the body from a smaller surface area, which is in contact with the body. The disks have diameters from approximately 2 millimeters or less to approximately 75 millimeters or more.

According to an embodiment of the present invention, the disks shapes at the interfaces to the individual's body or thermal packs can also be non-flat, including but not limited to semi-spherical, pyramidal, conical, concave, convex, bumped, or contain an array of smaller shapes, e.g. semi-spherical protrusions. Advantageously the protrusions move against the skin of the user creating a massaging sensation as the user moves.

The pins or rivets may be in the form of a variety of shapes. They may be oval or round, conical, concave, convex, bumped or may comprise an array of smaller shapes.

In one embodiment, the thermally conductive member comprises a powered massaging element in order to provide an enhanced sensation of relief. The massaging element may be delivered via a powered vibratory mechanism with an accompanying power source such as a battery.

In another embodiment, thermally conductive members are filled with an easily evaporating liquid and vapor of said liquid, with optional wicking material inside said thermally conductive members, so that the thermally conductive members operate as a heat pipe or heat pump to more effectively transfer thermal energy between the individual's body and the thermal pack.

In one embodiment, one or more pockets are also able to receive a vibratory pack in order to provide additional massaging sensations simultaneously with thermal treatment.

In the embodiment, a vibratory element is electrically powered and added either as a portion of the thermally conducting member; or as a separate pack to the pocket, it is delivered via a battery driven sub assembly; including one derived from the group consisting of piezo-vibrators, motorized vibrators, and electromagnetic based vibrators. In one embodiment, the belt may be fastened through a snap, buckle, button or Velcro means.

In another embodiment, an electronic temperature measurement and feedback device is installed in the belt. Temperature measurement and feedback device includes a temperature sensing electronic element such as a thermocouple, bi-metallic temperature sensitive element, resistance temperature detectors (RTDs), or similar, combined with an electronic circuit, an optional timer, a power source, such as battery, and an acoustic signal generating element, such as electric buzzer. The temperature-sensing element is installed in the proximity of at least one of thermally conductive members or is in direct contact with at least one thermally conductive member and is measuring the temperature of thermally conductive members.

The temperature measurement and feedback device generates an acoustic signal, providing belt operation information to the user or caregiver in a number of scenarios, including:
  (i) When the measured temperature exceeds a preset value, such a safe temperature value, for example, 42° C.;
  (ii) When the measured temperature drops below a preset safe value in case of a cooling pack, such as 15° C.;
  (iii) When the usage time at the given temperature exceeds safe time interval, for example 42° C. for 8 hours;
  (iv) When a pre-set time interval for continuous treatment is exceeded, for example 12 hours;
  (v) When the temperature drops below a pre-set value, for example below 38° C., in case of a heating pack, to indicate that the heating pack needs to be replaced;
  (vi) When the temperature raises above a pre-set value, for example above 35° C., in case of a cooling pack, to indicate that the cooling pack needs to be replaced.
  Different tones, amplitudes, frequencies, and sequences of the acoustic signal can be used to convey the information to the user or caregiver.

Thermal Packs

The thermal packs described for use in the invention herein are either disposable or reusable and may comprise those which deliver heat, a cooling sensation, or a combination thereof. In one embodiment, the thermal packs are alternatively described herein as "retainers", which can generate either a positive or negative temperature differential relative to a surrounding environment.

The thermal packs or retainers, which are capable of being placed into the pockets, can have different thermal profiles, including heating or cooling, thermal intensity or duration of action. In one embodiment, one set of pockets incorporates retainers that deliver heat from about 4 hours to about 6 hours; and one set of pockets can incorporates retainers that deliver heat from about 8 hours to about 12 hours. In one embodiment, one set of pockets incorporates retainers that deliver heat and one set of pockets incorporate retainers that deliver a cooling sensation.

In one embodiment, thermal packs are heating packs exemplified by bags, pouches, patches or compartments filled with an exothermic mixture, which is actuated by contact with air (i.e. oxygen) and or water. An example of this is one, which contains an iron-carbon mixture heating pack, which also typically contains water and a metal salt and heats upon contact with air.

In order to facilitate the thermal reaction when using exothermic heating packs, a sufficient air supply must be available to the heat packs. In one embodiment the garment, belt or more specifically, the pockets within the belt are constructed of a fabric, which comprises air-permeable materials. In another embodiment the belt or pockets comprise apertures in the fabric of the pocket and/or belt and are provided to ensure a sufficient air supply.

Another suitable type of heating pack is a catalytic oxidation-based heater, such as heater, which produces heat by catalytically oxidizing vapors of a volatile fuel such as ethanol or methanol, on a suitable catalyst such as platinum in the presence of air. In another embodiment the heating pack is an exothermic mixture pack containing a substance producing heat as a result of a reaction with water and carbon dioxide, for example calcium chloride.

In one embodiment, the thermal packs are electrically heated or electrically cooled packs, having a rechargeable battery and a thermal element, such as a resistive heater, or a thermoelectric based cooling and heating element such as Peltier element. In one embodiment, the electrically powered thermal packs are integrated devices of substantially flat rectangular, round, or elongated shape, with substantially flat rechargeable battery and substantially flat thermal element that is disposed on the surface of the battery creating an integrated sandwich-like structure of the electrically powered thermal pack.

In one embodiment, the shape or color of the pocket is designed to receive a pack that delivers one type of profile in order for the user to know which type of pack is intended to be inserted into one type of pocket. In this embodiment, the shape or color of the pocket is mated equally with the shape or color of the thermal pack (i.e. insert). Shapes of pockets and packs may include but are not limited to tapered shaped designs, triangle shaped designs, star shape designs, and oval or circular shaped designs. The pattern of the designs may be configured such that the shaped retainers deliver a customized or optimized type of thermal profile. In one embodiment, this pattern includes alternating heating and cooling packs in order to deliver a heating and cooling profile.

In one embodiment, the dimension of the thermal pack is from about 5 millimeters to about 200 millimeters. In another embodiment, the thermal pack is substantially flat with the thickness of the pack ranging from about 2 millimeters to about 10 millimeters, and the other dimensions of the pack ranging from about 10 millimeters to about 200 millimeters. The temperature for the delivery of heat for the treatment of muscle or joint pain through the skin is from about 35° C. to about 55° C. The optimal temperature depends on the desired length of treatment, area of contact, skin sensitivity in the treated area, and whether the temperature is measured on the skin, on the surface of the thermal pack, or on the surface of the thermally conductive members. In one embodiment, the temperature measured by a thermocouple inserted between the individual's skin and the thermally conductive member of this invention is 38° C., 40° C., 45° C., or 50° C.

The temperature for the delivery of cold for the treatment of muscle or joint pain through the skin is from about 5° C. to about 30° C. The optimal temperature depends on the desired length of treatment, area of contact, skin sensitivity in the treated area, and method of measurement, including whether the temperature is measured on the skin, on the surface of the thermal pack, or on the surface of the thermally conductive members. In one embodiment, the temperature measured by a thermocouple inserted between the individual's skin and the thermally conductive member of this invention is 5° C., 10° C., 20° C., 25° C., or 30° C.

Another suitable type of thermal pack is a catalytic oxidation-based heater, such as heater producing heat by catalytically oxidizing vapors of a volatile fuel, such as ethanol, on a suitable catalyst, such as platinum, in presence of air. Another type of thermal pack is an exothermic mixture pack containing a substance producing heat as a result of a reaction with water and or carbon dioxide, for example calcium hydroxide.

Another suitable type of thermal pack is a heater that is powered by a flammable fuel. In this pack the thermal pack is surrounded by a closable non-flammable thermally conductive material such as aluminum, iron, silver, steel or stainless steel; and is further packed with a wicking material. To operate the thermal pack, the wicking material is saturated with a flammable fuel such as but not limited to lighter fluid, kerosene, ethanol, methanol as well as fuels containing varying mixtures of propane, isobutane, and n-butane. In this embodiment, the wicking material is ignited and the lid of the self contained pack is closed upon use.

In another embodiment, the thermal packs or retainers contain substances that are capable of retaining heat for extended periods of time, such as thermal beads, encapsulated water, wax, phase changing materials, ceramics, sand, grains, rice, wheat, corn, etc. These thermal packs or retainers are externally heated in an oven, microwave, etc., and slowly release heat upon insertion into the belt.

In another embodiment, the thermal packs or retainers are microwaveable gel-filled packs such as those commercially available gel-packs.

In another embodiment, the thermal packs or retainers are cooling packs, which can be represented by bags, pouches, patches, or other compartments filled with substances which are capable of staying cold for extended periods of time, such as beads, encapsulated water, glycerin, urea, alcohol, oil, or similar, phase changing materials, ceramics, grains, etc.

In another embodiment, the thermal packs or retainers are freezable gel-filled packs such as those commercially available gel-packs.

In another embodiment, the thermal packs or retainers are self-contained electrically cooled packs, including a power supply, such as primary battery or rechargeable battery, a control means, such as on/off switch, and a cooling element, such as Peltier cooling element.

In another embodiment, the thermal packs or retainers generate low temperatures and provide cooling effect using evaporative cooling, whereby a volatile fluid such as ethanol is allowed to slowly evaporate from a pouch, bad, or container, resulting in the cooling effect.

According to another embodiment of the present invention, thermally conductive members are represented by sealed liquid filled pouches filled by water, silicone oil, other liquids or semi-solid materials or gels, said pouches interfacing to the patient's body and to the thermal packs. In one embodiment, liquid-filled pouches are sewn into the elastic belt. In another embodiment, thermally conductive members comprise thermally conductive rubber elements interfacing to the patient's body and to the thermal packs.

Methods of Delivery

Since the thermal packs or retainers can be inserted into a multitude of pockets in the belt, cold and hot treatments can be delivered either simultaneously or sequentially, allowing for a wide range of combinations and treatment options. One advantage of this lies in the ability to avoid overheating or overcooling certain areas of the body resulting in potential undesirable side effects of thermal therapy. Another advantage of this invention lies in the ability to avoid sensitization on any one part of the body that may be exhibit numbness, loss of sensation or loss of pain relief efficacy. If any one body part does become sensitized the invention described herein allows for switching of the type of thermal pack (i.e. hot to cold), the intensity of the thermal pack (i.e. low to medium to high); or the duration of the thermal pack. The duration can be described as short, i.e. less than 4 hours, medium; i.e. 4 hours to 8 hours, and long; i.e. longer than 8 hours. A thermal pack may also be switched out with a vibratory pack or a vibratory pack can be added to a pocket into which a thermal pack is already inserted.

In one embodiment the individual may use an exothermic thermal pack for heat treatment during one period, and use cooling thermal packs during a second treatment period. In another treatment the individual may use heating and cooling packs simultaneously. In one embodiment the belt comprises pockets in a checkerboard pattern allowing for an alternating pattern of packs with various treatment delivery types (i.e. heating, cooling, and massage).

Incorporation of a Topical Agent

In one embodiment, the thermal pack or retainer comprises a portion of the pack that contains a liquid topical agent that is delivered through a channel in the thermally conductive member onto the skin. The topical may be a medicinal counter-irritant such as an external analgesic, a chemical topical heating agent, a heating sensate or a tingling sensate. Suitable external analgesics include but are not limited to those disclosed in the Tentative Final Monograph for External Analgesic Drug Products for over-the-counter human use, U.S. Federal Register Vol. 48, No. 27, Feb. 28, 1983. These monographed external analgesics include counter-irritants that produce redness, for example, Allyl isothiocryanate 0.5-5%, Methyl salicylate 10-60%, and Turpentine oil 6-50%; Irritants that produce cooling, for example, Camphor >3% to 11%, or Menthol 1.25-16%; Irritants that produce vasodilatation, for example Histamine dihydrochloride 0.025-0.10%, or Methyl nicotinate 0.25-1%; and irritants that do not produce redness, for example, Capsaicin 0.025-0.25%, Capsicum containing 0.025-0.25% capsaicin, or Capsicum oleoresin containing 0.025-0.25% capsaicin.

Suitable non-monograph cooling sensates are selected from the group including but are not limited to [(−)-isopulegol, (2S)-3-(l-menthoxy)propane-1,2-diol, "Frescolat MGA"/menthone glycerin acetal, "Frescolat ML"/menthyl lactate, "WS-14"/N-t-butyl-p-menthane-3-carboxamide, "WS-23"/2-Isopropyl-N,2,3-trimethylbutyramide, WS-12/N-(4-methoxyphenyl)-p-menthane-3-carboxamide, "WS-3"/N-Ethyl-p-menthane-3-carboxamide, and "WS-5"/Ethyl 3-(p-menthane-3-carboxamido)acetate].

We claim:
1. A therapeutic device comprising
   a) a conformable and reusable portion having an inside surface and an outside surface;
   b) at least one pocket on the conformable and reusable portion;
   c) at least one retainer, wherein the at least one retainer sits in the at least one pocket and wherein the at least one retainer comprises a mixture of chemical substances that react chemically to produce an exothermic effect, wherein the mixture of chemical substances heats relative to a surrounding environment;
   d) at least one conductive member that protrudes from the inside surface of the conformable and reusable portion, wherein the at least one conductive member is in contact with the body of the user, either directly contacting the skin, or contacting the body of the user through clothing or garments worn by the user, wherein the at least one conductive member is in contact with the at least one retainer and transmits heat from the at least one retainer to the body of the user, wherein the at least one conductive member is shaped as a first disk and a second disk interconnected by a cylindrical element, wherein the first disk is in contact with the at least one retainer, wherein the second disk interfaces with the body of the user, and wherein the first disk has a larger surface area than the second disk.

2. The therapeutic device of claim 1 wherein the at least one retainer heats through the at least one conductive member.

3. The therapeutic device of claim 1 wherein the at least one conductive member is made, at least in part, from a metal selected from the group consisting of aluminum, copper, silver, steel and metal alloys of aluminum, copper, silver and steel and combinations thereof.

4. The therapeutic device of claim 1 wherein the at least one conductive member is made, at least in part, from conductive fabrics, composites, plastics, polymers, rubber, ceramics and mixtures thereof.

5. The therapeutic device of claim 1, wherein the at least one pocket has substantially a same shape as the retainer.

6. The therapeutic device of claim 1, wherein the conformable and reusable portion conforms to fit over the shoulder, back, knee, or elbow of a human.

7. The therapeutic device of claim 1, wherein the at least one conductive member is a sealed liquid filled pouch.

8. The therapeutic device of claim 1, wherein the therapeutic device comprises at least two conductive members and at least two retainers, wherein at least a first conductive member and a first retainer delivers heating or cooling for 4 to 6 hours and at least a second conductive member and a second retainer delivers heating or cooling for 8 to 12 hours.

9. The therapeutic device of claim 1, wherein the mixture of substances comprises iron powder.

* * * * *